United States Patent
Yokoyama et al.

(10) Patent No.: US 7,002,674 B2
(45) Date of Patent: Feb. 21, 2006

(54) METHOD AND APPARATUS FOR INSPECTING DEFECTS

(75) Inventors: Hirokazu Yokoyama, Osaka (JP); Hiroki Murakami, Tokyo (JP)

(73) Assignee: Sumitomo Mitsubishi Silicon Corporation, Tokyo (JP)

( * ) Notice: Subject to any disclaimer, the term of this patent is extended or adjusted under 35 U.S.C. 154(b) by 324 days.

(21) Appl. No.: 10/423,904

(22) Filed: Apr. 28, 2003

(65) Prior Publication Data

US 2003/0227620 A1    Dec. 11, 2003

(30) Foreign Application Priority Data

Jun. 7, 2002   (JP)  ............................. 2002-167005

(51) Int. Cl.
*G01N 21/88* (2006.01)
(52) U.S. Cl. .................................................. 356/237.2
(58) Field of Classification Search .. 356/237.1–237.6, 356/600–613; 438/14–16; 355/27
See application file for complete search history.

(56) References Cited

U.S. PATENT DOCUMENTS 6,812,045 B1 * 11/2004 Nikoonahad et al. ......... 438/14

2002/0027653 A1 * 3/2002 Shibata et al. ........... 356/237.3

FOREIGN PATENT DOCUMENTS

| JP | 06-121314 | 2/1994 |
|----|-----------|--------|
| JP | 09-085625 | 3/1997 |
| JP | 10-109401 | 4/1998 |
| JP | 10-176716 | 6/1998 |
| JP | 11-371957 | 12/1999 |
| JP | 2000-231352 | 7/2000 |

* cited by examiner

Primary Examiner—Tu T. Nguyen
(74) Attorney, Agent, or Firm—Bacon & Thomas, PLLC

(57) ABSTRACT

Provided are a method and apparatus for inspecting a defect on a plane, such as a surface or a section, of an object to be inspected. The object is, for instance, a silicon wafer. A whole area of a plane of the object is first imaged by an optical system to gain image signals. Then, a particular region on the plane is positionally detected from the image signals. The particular region includes a blot and a defect and has a higher luminance than a remaining region on the plane. A blot is distinguishably detected from the particular region. A specified region on the plane is then subjected to a detailed inspection under a microscope. The region is set to avoid the blot even if the blot is on the region. The detailed inspection under the microscope is performed toward only the region with no blot.

4 Claims, 6 Drawing Sheets

BLOT-DETECTED IMAGE(AFTER BINARIZATION)

BINARY IMAGE(AFTER BINARIZATION)

ORIGINAL IMAGE(BEFORE BINARIZATION)

METHOD AND APPARATUS FOR INSPECTING DEFECTS

BACKGROUND OF THE INVENTION

1. Technical Field of the Invention

The present invention relates to a method and an apparatus for inspecting defects on a surface or section of an object to be inspected, such as a silicon wafer.

2. Related Art

A microscopic inspection for possible detects on a surface or section of an object to be inspected, such as a silicon wafer, has already been carried out. Because the field of view of a normally used microscope is approximately a several-millimeters square, inspecting a whole area of a surface to be inspected, for example, of a silicon wafer requires that the field of view of the microscope be moved several tens of times or several hundreds of times repeatedly. Thus it takes a lot of time for an operator to perform the inspection.

The technique for overcoming such a situation has been proposed by Japanese patent laid-open (unexamined) publications 11(1999)-354599 and 2001-183301.

In the former publication, a differential interference microscope with an objective lens is used. At first, with the magnification of the objective lens adjusted to a lower value, a one-dimensional CCD camera is operated to image a surface of a silicon wafer through a wider inspection field of view. Coordinates of luminescent spots detected by an optical system are recorded for inspecting the whole surface of the silicon wafer. Secondary, the magnification of the objective lens is changed to a higher value and the positions of the luminescent spots that have been detected by the optical system are imaged. The resultant image is used for a defect inspection. This inspection technique makes it possible to omit the locations having no defects from being imaged and inspected, whereby the inspection time can be shortened.

The inspection technique disclosed by the latter publication is realized by using two optical systems. Concretely, the two optical systems for both of a bright view and a dark view are placed for imaging, in which on the basis of the positions of defects detected in the dark field, a bright-field image at the positions is displayed for the inspection.

However, the inspection techniques disclosed by the above two publications have still difficult situations as below. In the case of the technique according to the publication 11(1999)-354599, the one-dimensional CCD camera installed in the differential interference microscope is used to image a surface of the silicon wafer or others. This results in that one field of view is not less than a square of a few millimeters, even if the magnification of the objective lens is adjusted to a lower value to widen the filed of view for imaging. Hence, this inspection technique has still suffered from the problem that it takes a lot of time to scan the whole area of a surface to be inspected of an object such as a silicon wafer.

In addition, when blots or others on an object, which are produced during, for example, an etching operation, are observed at a higher magnification, the blots or others are imaged as being luminescent spots. This makes it difficult to distinguish the blots or others from the defects. As a result, during a final inspection step carried out at higher magnifications, there often occurs the necessity of re-imaging the whole area of the surface of the object, which will reduce the efficiency of inspection.

On the other hand, the technique according to the publication 2001-183301 has been realized by adopting two different optical systems, where the inspecting magnifications assigned to the optical systems are approximately equal to each other, thus increasing detection sensitivity. However, since the inspection time is about two times longer than the conventional detection systems, the efficiency of inspection is suppressed to lower values, which makes it difficult to apply this detection technique to practical use.

SUMMARY OF THE INVENTION

The present invention has been attempted to break through the foregoing current situations, and an object of the present invention is to provide a method and apparatus for inspecting defects, which have the capability of performing the inspection in a shorter time and with efficiency.

In order to achieve the above object, as one aspect of the present invention, there is provided a method of inspecting a defect of an object to be inspected, comprising the steps of: performing a first inspection in which a whole area of the plane of the object is subjected to imaging with the use of an optical system to gain image information in relation to the plane, and then to positional detection of a particular region on the plane on the basis of the image information, the particular region having a higher luminance than a remaining region on the plane; and performing a second inspection in which the plane of the object is subjected to a detailed inspection under a microscope with reference to information indicative of a position of the particular region detected by the first inspection.

Preferably, the plane consists of either a surface or a section of the object to be inspected and the particular region consists of either a defect or a blot on either the surface or the section.

Still preferably, the first inspection performing step includes the steps of: binarizing the image information imaged by the optical system, whereby a luminance distribution being the particular region is provided; and detecting a blot from the luminance distribution depending on a reference area size previously set to the luminance distribution, while the second inspection performing step includes the steps of: determining whether or not the blot exists on the microscopic-inspecting area; specifying a microscopic-inspecting area on the plane of the object if it is determined that the blot exists on the microscopic-inspecting area, the microscopic-inspecting area being formed by positionally avoiding the blot on the plane; and applying, to the detailed inspection under the microscope, the microscopic-inspecting area specified on the plane of the object.

It is also preferred that another area is equal in an area size to and juxtaposed to the blot.

Accordingly, in the first inspection, the whole area of a plane, such as a surface, of an object to be inspected (such as a silicon wafer) is imaged by means of the optical system for acquiring image signals, and then, from image signals, a defect and/or a blot are positionally detected. That is, prior to a microscopic inspection of a predetermined region on the plane of the object, the whole area of the plane is subjected to imaging carried out by the optical system with no microscope. The optical system is able to provide an image of which field of view is remarkably larger than that provided by the microscope. Although it is impossible to know the shape of each blot from the image, applying adequate types of imaging processing to the image allows a defect to be detected as luminescent spots and allows a blot to be detected as a luminance distribution having a certain area size. This detection will therefore lead to the determination whether or not there are blots and/or defects, so that, if there are blots and/or defects, the coordinates of the blots and/or defects are memorized for re-specifying a microscopic-inspecting region used in the second inspection.

In the second inspection, based on the positional information about the blots and/or defects found through the first inspection, a microscopic-inspecting region on the plane is subjected to a detailed inspection under the microscope. Practically, in cases where there is a blot(s) that has an area size larger than a predetermined value and exists partially or entirely so as to be overlaid on the microscopic-inspecting region on the plane, the microscopic-inspecting region is positionally adjusted, prior to performing the microscopic inspection. For example, the microscopic-inspecting region is partially or entirely shifted from its original position to avoid the blot(s) based on a predetermined algorithm in an automatic fashion. Accordingly, the blot will not be involved into the microscopic inspection. On the other hand, there is a defect(s) on the plane of the object, the microscopic inspection is directed to only the defect. It is therefore possible to reduce the inspection time.

As described above, an image acquired by photographing the entire area of a plane of an object is first subjected to processing to detect the positions of defects and/or blots, without using a microscope. And based on detected positional results, locations to be inspected are re-specified on the plane, before being subjected to an actual inspection under the microscope. An inspection performance can therefore be improved and the entire inspection time can be shortened.

In particular, a blot(s) can be detected positionally in the first inspection, and a microscopic-inspecting region that has been re-specified to avoid the blot can be inspected under the microscope in the second inspection. This technique is especially effective for improving the inspection performance and shortening the inspection time.

Still, it is preferred that the object has a width and a length; and wherein the first inspection performing step includes the steps of: placing, as part of the optical system, a one-dimensional CCD camera of which field of view is set to agree with the width of the object, and driving at least one of the object and the CCD camera to cause a relative movement between the object and the CCD camera so that a whole area of the plane of the object is imaged, the relative movement covering a specific distance corresponding to the length of the object.

According to this configuration, it is sufficient to move the one-dimensional CCD camera for a distance corresponding to the length of the object. This allows the entire imaging of a plane (a surface or a section) of the object to be imaged easily in a shorter time. Image signals acquired in such a way can immediately be used in the second inspection.

As another aspect of the present invention, there is provided an apparatus for inspecting a defect of an object to be inspected, comprising: an optical system used for imaging a whole area of a plane of the object to be inspected, to gain image information in relation to the plane, and positionally detecting a particular region on the plane on the basis of the image information, the particular region having a higher luminance than a remaining region on the plane; and a microscope used for a detailed inspection of the plane of the object with reference to information indicative of a position of the particular region detected with the use of the optical system.

By way of example, the plane consists of either a surface or a section of the object to be inspected and the particular region consists of either a defect or a blot on either the surface or the section.

It is preferred that the defect inspection apparatus further comprises a processor configured to functionally perform: binarizing the image information imaged by the optical system, whereby a luminance distribution being the particular region is provided; detecting a blot from the luminance distribution depending on a reference area size previously set to the luminance distribution; determining whether or not the blot exists on the microscopic-inspecting area; specifying a microscopic-inspecting area on the plane of the object if it is determined that the blot exists on the microscopic-inspecting area, the microscopic-inspecting area being formed by positionally avoiding the blot on the plane; and applying, to the detailed inspection under the microscope, the microscopic-inspecting area specified on the plane of the object.

Another preferred example is that another area is equal in an area size to and juxtaposed to the blot.

It is preferred that the object has a width and a length and the optical system has a one-dimensional CCD camera of which field of view is set to agree with the width of the object.

It is still preferred that the processor is configured to drive at least one of the object and the CCD camera to cause a relative movement between the object and the CCD camera so that a whole area of the plane of the object is imaged, the relative movement covering a specific distance corresponding to the length of the object.

Preferably, the defect inspection apparatus further comprises a unit that is configured to drive at least one of the object and the CCD camera to cause a relative movement between the object and the CCD camera so that a whole area of the plane of the object is imaged, the relative movement covering a specific distance corresponding to the length of the object.

The configurations of the defect inspection apparatus areaso able to provide the identical or similar operations and advantages to those obtained by the defect inspection method of the present invention described already.

DETAILED DESCRIPTION OF THE PREFERRED EMBODIMENT

Referring to the accompanying drawings, a preferred embodiment of the present invention will now be described.

Figure 1:
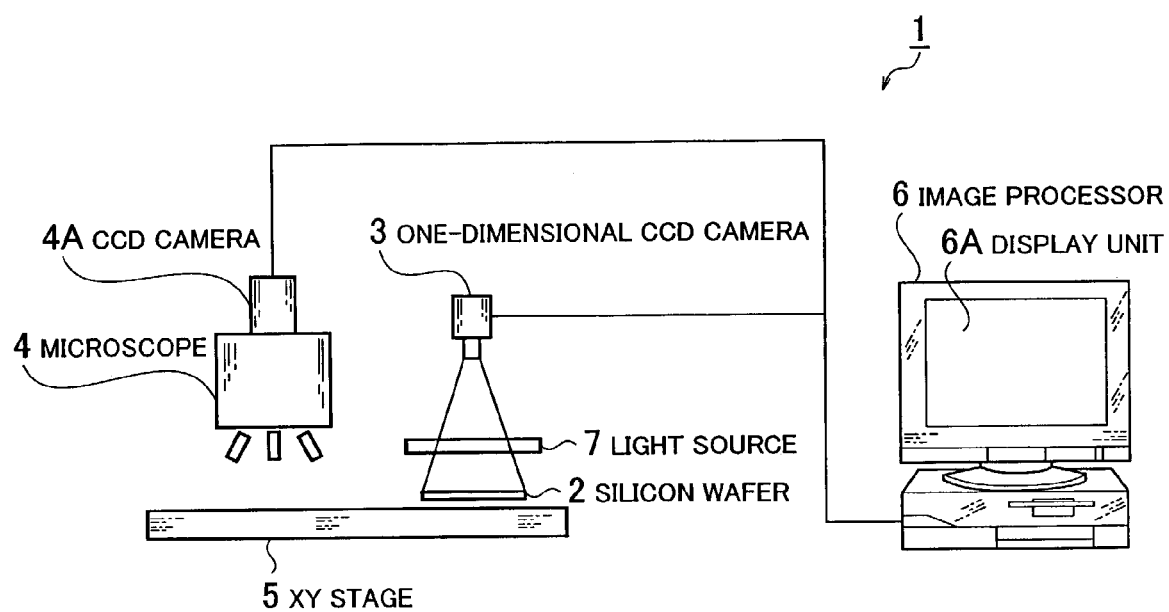
FIG. 1 shows the configuration of a defect inspection apparatus according to an embodiment of the present invention.
Figure 2A:
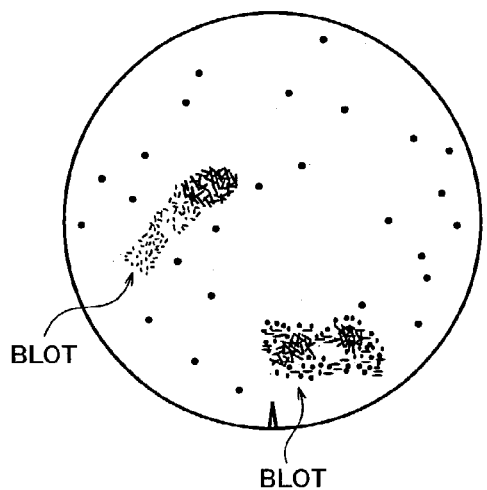
FIGS. 2A to 2D are illustrations each showing an image of a surface to be inspected of a silicon wafer.
Figure 2B:
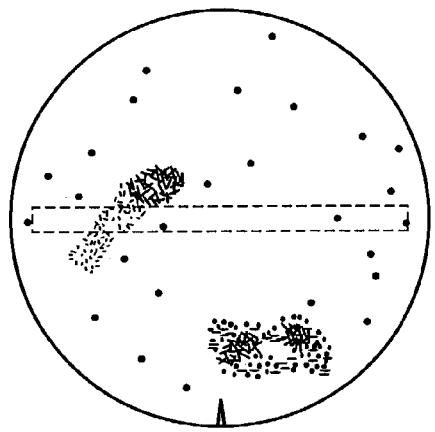
Figure 3:
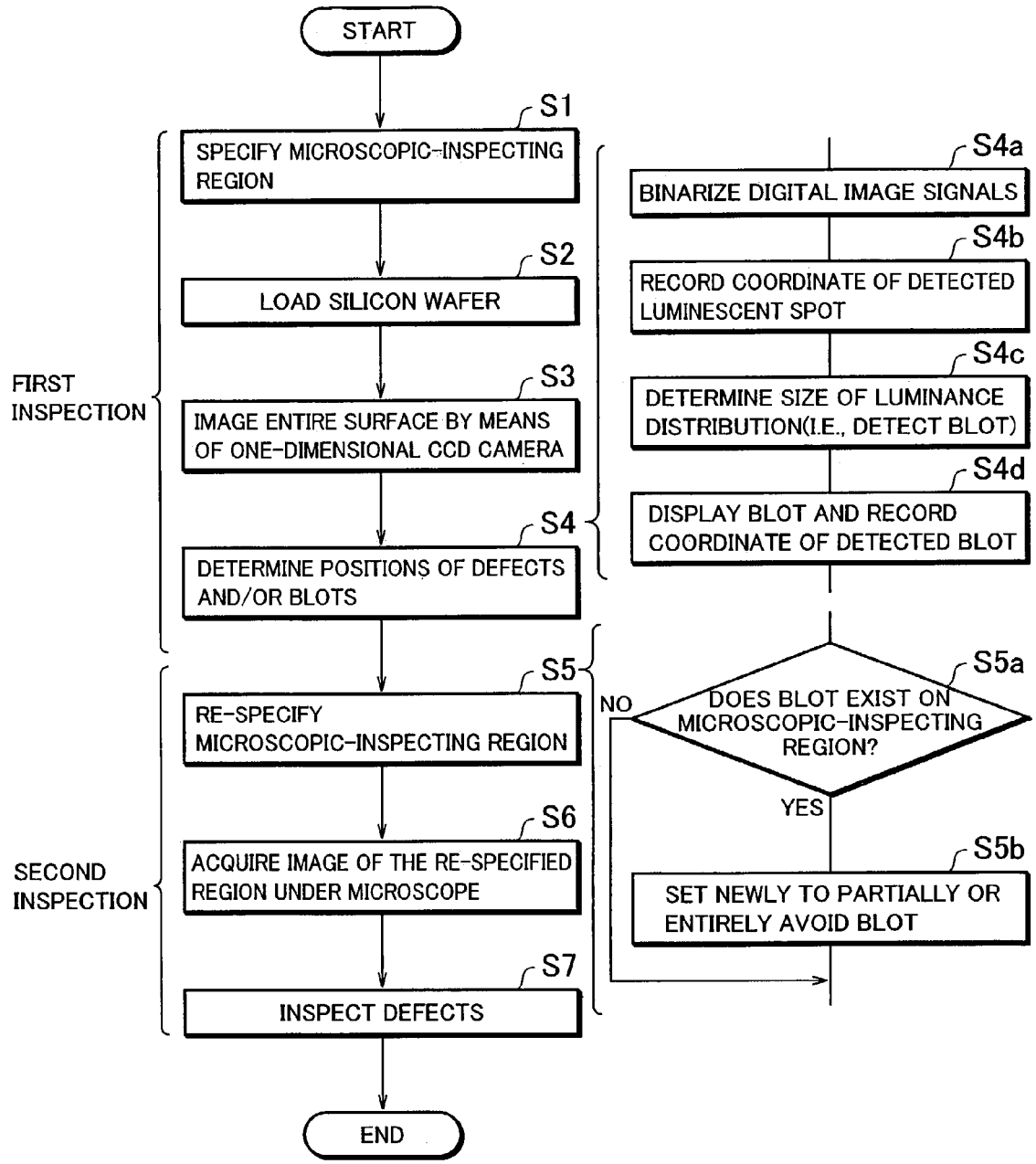
FIG. 3 is a flowchart outlining how to inspect defects on the surface of the silicon wafer.
Figure 4:
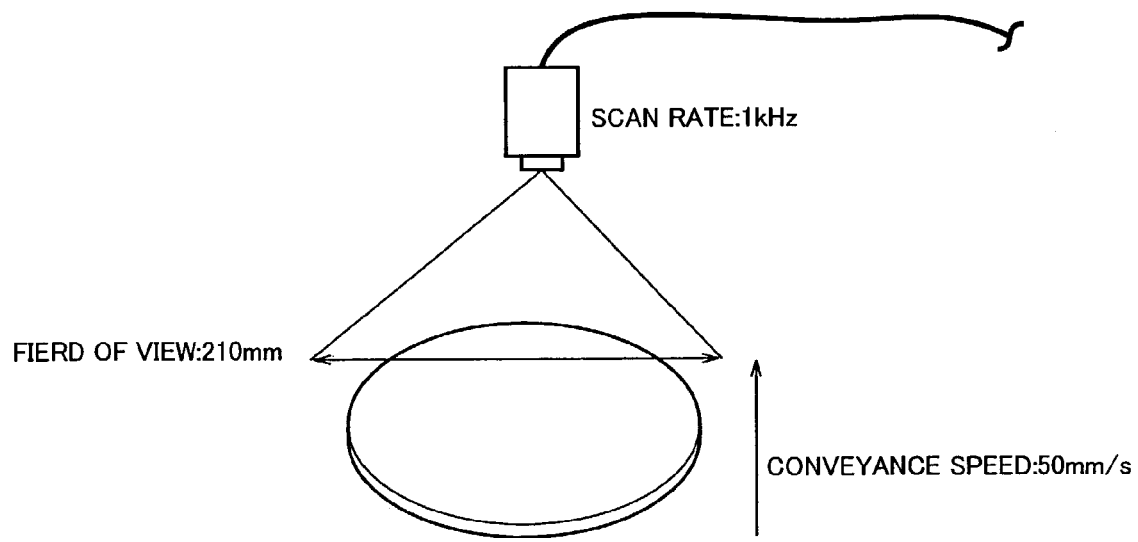
FIG. 4 pictorially exemplifies a one-dimensional CCD camera according to the embodiment of the present invention.
Figure 5:
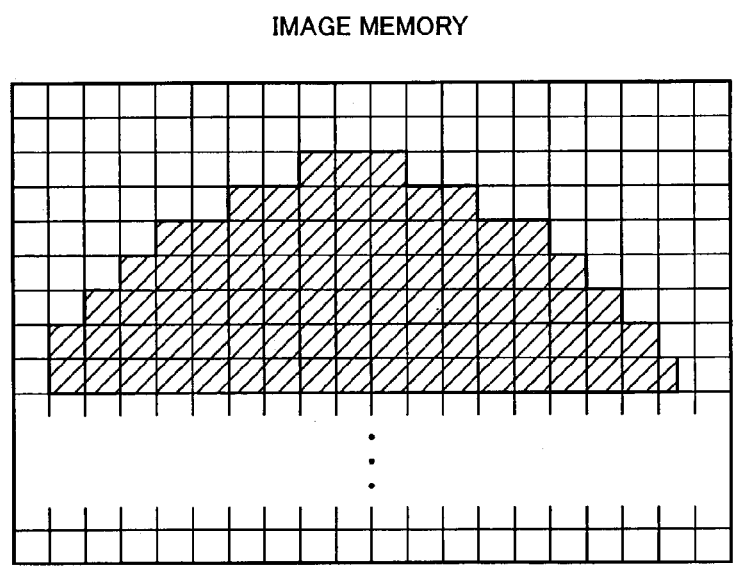
FIG. 5 exemplifies the configuration of an image memory according to the embodiment of the present invention.
Figure 6:
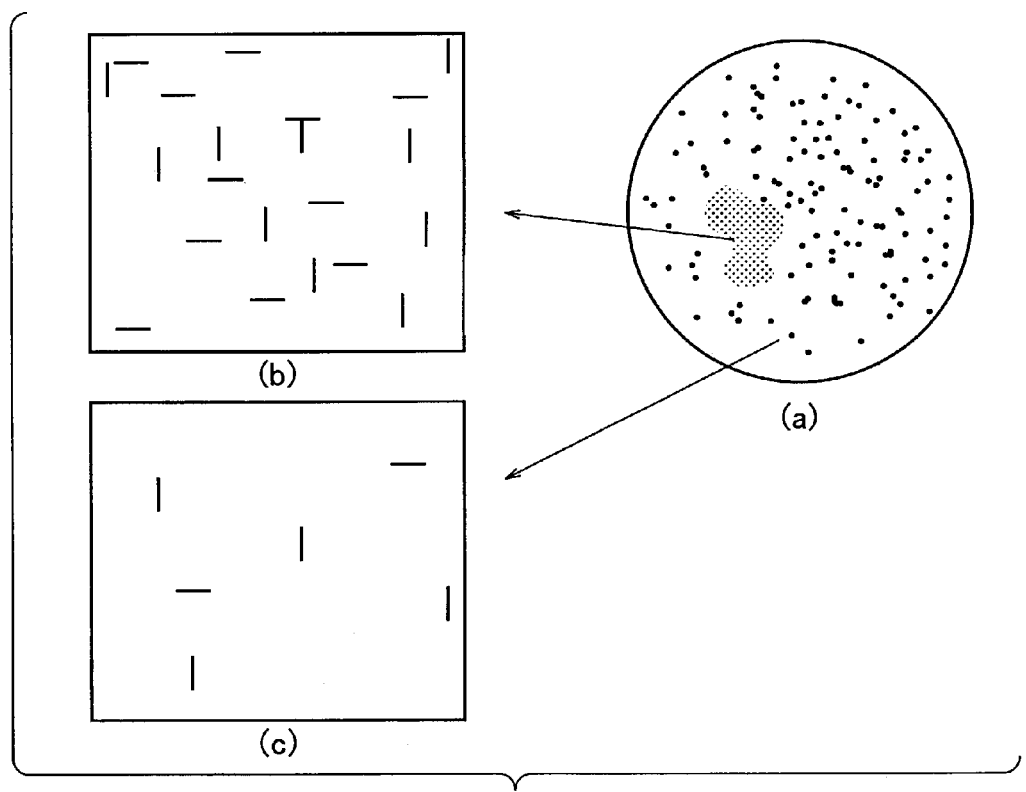
FIG. 6 pictorially shows an entire image and enlarged images of the surface of the silicon wafer.
Figure 7C:
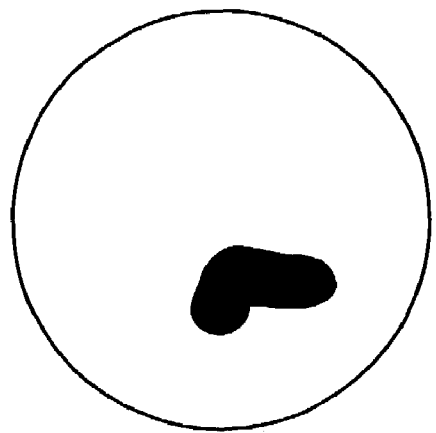
FIGS. 7B and 7C illustrate images of the surface of the silicon wafer, which have been processed according to the present embodiment.
Figure 7B:
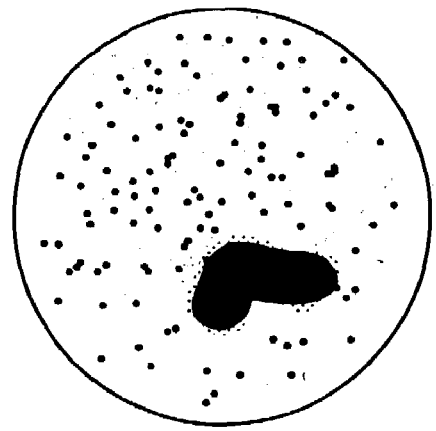
Figure 7A:
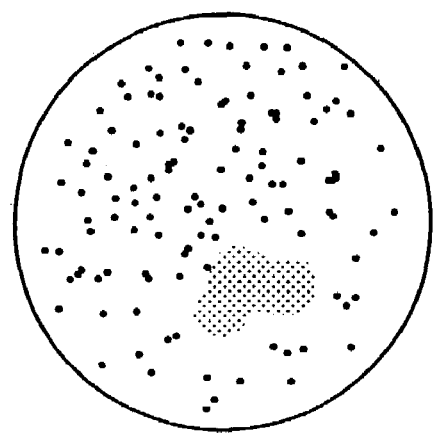
FIG. 7A illustrates an original image of the surface of the silicon wafer.

FIG. 1 shows the configuration of a defect inspection apparatus according to the present embodiment; FIGS. 2A to 2D are illustrations each showing an image of a surface to be inspected of a silicon wafer; FIG. 3 is a flowchart showing how to inspect defects on the surface of the silicon wafer; FIG. 4 illustrates a one-dimensional CCD camera; FIG. 5 exemplifies the configuration of an image memory; FIG. 6 pictorially shows an entire image and enlarged images of the surface of the silicon wafer; and FIGS. 7A to 7C illustrate images of the surface of the silicon wafer, which show various types of processing applied to the original image in the present embodiment.

(Defect Inspection Apparatus)

First of all, a defect inspection apparatus for carrying out a defect inspection method will be described. As shown in FIG. 1, a defect inspection apparatus 1 is equipped with a one-dimensional CCD camera 3, a microscope 4, an XY stage 5, and an image processor 6.

The one-dimensional CCD camera 3 is placed to carry out the first inspection. In the first inspection, the whole area of a plane to be inspected, such as a surface or a section, of a silicon wafer 2 is imaged, so that image signals are acquired. Then, from the image signals, the position(s) of a defect(s) and/or a blot(s) is detected. The silicon wafer 2 is one example of objects to be inspected.

The one-dimensional CCD camera 3 has a field of view that agrees with the width (diameter) of the silicon wafer 2 and is made to move for a distance that corresponds to the length (diameter) of the silicon wafer 2. Thus the one-dimensional CCD camera 3 will travel relatively to the silicon wafer 2.

The CCD camera 3, to which a microscope is not attached, is loaded with an optical-system lens (such as a TV camera lens). Hence, this optical-system lens allows the whole area of a surface of the silicon wafer 2 to be imaged. Resultant image signals indicative of an image are converted into digital signals, which are then sent to the image processor 6.

The microscope 4 is placed for the second inspection dedicated to a detailed microscopic inspection of the surface of the silicon wafer 2. The detailed microscopic inspection is carried out on the basis of positional information of a defective portion(s) and/or a blot(s) detected under the one-dimensional CCD camera 3. A one-dimensional or two-dimensional CCD camera 4A is attached to this microscope 4. This CCD camera 4A is coupled with the image processor 6. Thus, image signals that have been detected by the microscope 4 from a microscopic inspecting region on the surface of the silicon wafer 2 are converted by the CCD camera 4A to digital signals, which are then sent to the image processor 6.

The XY stage 5 is responsible for making the silicon wafer 2 travel in both X- and Y-directions. That is, the XY stage 5 is configured to move the silicon wafer 2 loaded thereon two-dimensionally (in both the X- and Y-directions) in a controlled manner, so that a microscopic inspecting region on a surface of the silicon wafer 2 and the surface thereof are made to positionally match to a field of view of the one-dimensional CCD camera 3 and the microscope 4, respectively. More specifically, the XY stage 5 conveys the silicon wafer 2 loaded there on so that the surface of the silicon wafer 2 is scanned by the one-dimensional CCD camera 3. The distance along which the XY stage 5 is moved, which is needed for the scanning under the CCD camera 3, is set to an amount slightly larger than the diameter of the silicon wafer 2. Hence under the operation of the XY stage 5, the silicon wafer 2 is moved at a faster speed throughout the distance slightly larger than the diameter of the silicon wafer 2. This makes it possible to image the whole area of a surface of the silicon wafer 2 in a shorter time under the one-dimensional CCD camera 3.

In addition, the XY stage 5 is driven to convey the loaded silicon wafer 2 to a position located immediately under the microscope 4, and then made to move the silicon wafer 2 in both the X- and Y-directions on a controlled sequence for inspection under the microscope 4. This sequential movement of the silicon wafer 2 in both the X- and Y-directions will allow each of grid-like microscopic inspecting regions on the surface of the silicon wafer 2 to come under the inspection view of the microscope 4 in turn. As a result, each grid-like microscopic inspecting region on the silicon wafer 2 is subjected to the inspection under the microscope 4.

Closely to the XY stage 5 is placed a loader (not shown). The loader operates to load or unload the silicon wafer 2 onto or from the XY stage 5.

The image processor 6 functions as means for processing image signals taken from both of the one-dimensional CCD camera 3 and the CCD camera 4A attached to the microscope 4. In detail, the image processor 6 binarizes image signals imaged by the one-dimensional CCD camera 3 to acquire a distribution of luminance on the silicon wafer 2, and determines whether or not the luminance distribution is over a predetermined area size. If the luminance distribution is over the predetermined area size, the image processor 6 concludes that the luminance distribution is a blot residing on the silicon wafer 2. The above determination for the luminance distribution makes it possible to judge if or not there is one or more blots on the silicon wafer 2. In cases where it is determined that one or more blots are present on the silicon wafer 2, control is made such that, during a detailed inspection under the microscope 4, the blots are removed from the regions to be microscopically inspected in an automatically fashion and regions other than the determined blot(s) on the silicon wafer 2 are microscopically inspected in detail.

The image processor 6 is coupled with the one-dimensional CCD camera 3, the CCD camera 4A attached to the microscope 4, a driver for the XY stage 5, and another driver for the loader, respectively. Accordingly, the image signals acquired by each of the one-dimensional CCD camera 3 and the CCD camera 4 attached to the microscope 4 are sent to the image processor 6. In addition, the image processor 6 issues, to the drivers, commands to control the operations of both the XY stage 5 and the loader according to an appropriately predetermined sequence. An operator gives the image processor 6 information indicative of a microscopic-inspecting region in which a defect inspection is desired on a silicon wafer 2 to be inspected. In response to the operator's setting of the region, the image processor 6 will enable the XY stage 5 to be driven such that the microscopic-inspecting region on the silicon wafer 2 loaded on the XY stage 5 is moved under the inspection view of each of the one-dimensional CCD camera 3 and the CCD camera 4A attached to the microscope 4.

The image processor 6 also applies the binarization processing to the image signals from the one-dimensional CCD camera 3 and the CCD camera 4 attached to the microscope 4. Accordingly, through a various types of processing including such binarization, the image processor 6 operates to display the image signals as an image on which one or more defects can be visualized distinctively. In order to achieve this display, the image processor 6 is equipped with a display unit 6A, on which image information including images that have been processed is provided.

To achieve the above various types of operation, the image processor 6 is provided with a variety of components that includes a CPU (central processing unit) in charge of the performance of a defect inspection method later described, and one or more memories. Stored into such memories are pieces of information indicating defects and/or blots that have been detected, the coordinates of the detected defects and/or blots, and a program for functionally realizing the defect inspection method later described.

(How to Inspect Defective Portions)

Referring to a flowchart shown in FIG. 3, a method of inspecting defects, which is carried out by the foregoing defect inspection apparatus 1, will now be described.

First, an operator gives various kinds of information to the image processor 6. Responsively, the signal processor 6 receives operator-inputting information specifying a desired microscopically-inspecting region and the size of a silicon wafer 2 which is an object to be inspected, and then determines a microscopically-inspecting region on the silicon wafer 2 (step S1 in FIG. 3). Then, under the control of the image processor 6, the loader makes the silicon wafer 2 load onto the XY stage 5 (step S2).

The image processor 6 then allows the XY stage 5 to be driven such that the silicon wafer 2 is conveyed to be located at a position immediately under the one-dimensional CCD camera 3, and then moved for a distance corresponding to the diameter of the silicon wafer 2 (step S3). Accordingly, as shown in FIG. 2A, the entire area of a surface to be inspected of the silicon wafer 2 is imaged. The resultant digital image signals are then taken into the signal processor 6.

From the digital image signals imaged by the one-dimensional CCD camera 3, one or more defects and/or one or more blots are positionally specified (step S4).

Practically, in the image processor 6, binarization is applied pixel by pixel to the acquired image signals, so that a defect(s) and/or a blot(s) are detected on a pixel basis as a luminescent spot(s) (step S4a). The luminescent spot that has been found is considered a defect and its coordinate is stored together with the processed image signals (step S4b).

If the luminescent spots at a plurality of pixels gather and make a distribution of luminance that spreads over a certain area, such distribution of luminance can be regarded as being a blot or a defective portion in which a defect occurs densely. Whether each distribution of luminescence is a defective portion or a blot is thus determined based on its area size. Area sizes that serve as criteria for the determination are set previously. To be specific, the area sizes are set to include all possible sizes of blots which may be brought about on silicon wafers 2, in cases where such silicon wafers 2 is manufactured under normal conditions.

Hence, in the image processor 6, it is determined whether or not a detected luminance distribution is below the criteria (area sizes to be referenced), which leads to the determination that the luminance distribution is a defective portion or a blot (step S4c). That is, if a luminance distribution is smaller in area size than all the criteria, the determination is made such that the luminance distribution is a defect, while if the opposite determination to the above comes out, the determination that the luminance distribution is a blot is made.

Figure 2C:
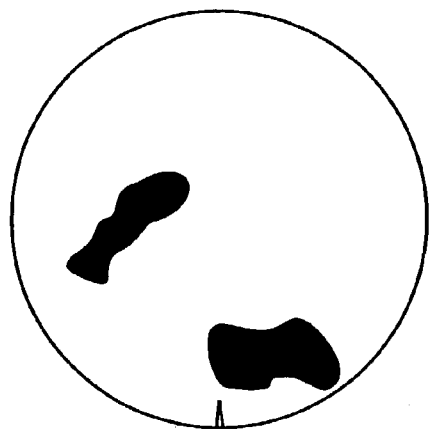

One or more blots detected through the above image processing is then subject to the display as shown in FIG. 2C, with the detected coordinates of the blots memorized (step S4d).

By the image processor 6, a microscopic-inspecting region on the silicon wafer 2 is re-specified using a remaining region other than the detected blot(s) (step S5).

For inspecting silicon wafers, a particular region on each silicon wafer that should be viewed under a microscope is decided beforehand. As exemplified by a dotted rectangle in FIG. 2B, such particular regions for the microscopic inspection include a variety of types of region decided dependently on the inspection standard. In the case that the blot(s) detected at step S4 is present partly or entirely in a microscopic-inspecting region, the existence will result in erroneously inspected results.

Therefore, to overcome this inconvenient situation, the image processor 6 determines whether or not the blot is partially or entirely located on the microscopic-inspecting region specified already on the surface of the silicon wafer 2 (step S5a). If this determination reveals that the blot is partially or entirely located on the once-specified microscopic-inspecting region, the microscopic-inspecting region is newly re-specified to positionally avoid the detected blot(s) (step S5b).

Figure 2D:
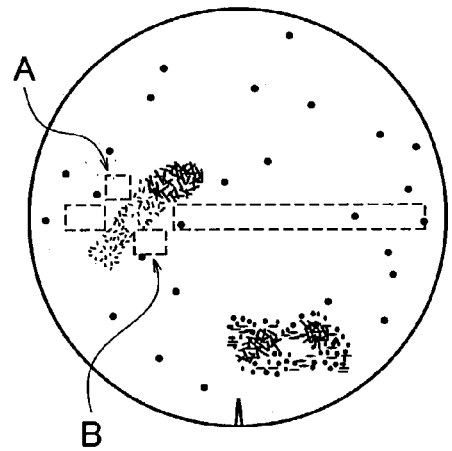

Practically, as shown in FIG. 2D, when a blot is present to partially overlap on a desired microscopic-inspecting region, the microscopic-inspecting region is partially shifted to a new location that may include other regions (A, B) avoiding the partially overlapped original blot ranges. The other regions (A, B) that have been newly specified, which do not include blots at all, has an area equal to the original regions and is positionally closed to the originals ones.

In the above configuration, a microscopic-inspecting region has been re-specified to avoid the original blot areas, but if the number of defects is a few, it may be possible that the microscopic-inspecting region is limitedly set to only an area that includes defects.

Under the control of the image processor 6, the XY stage 5 is then driven to allow the silicon wafer 2 to be conveyed so as to be positioned immediately under the microscope 4, and the microscopic inspecting region that has been re-specified is imaged through the microscope 4 (step S6). That is, the XY stage 5 is driven to move the silicon wafer 2 along the microscopic-inspecting region that has been re-specified at step S5, so that the microscopic-inspecting region is imaged by the CCD camera 4A attached to the microscope 4.

An image acquired by the CCD camera 4A is then taken into the image processor 6, and possible defects within the microscopic-inspecting region that has been re-specified on the silicon wafer 2 is inspected (step S7).

In the present embodiment, the processing at steps S1 to S4 is categorized into the first inspection, while the processing at steps S5 to S7 is categorized into the second inspection.

(Advantages)

As described above, an image acquired by imaging the entire area of the silicon wafer 2 is first subjected to processing to detect the positions of defects and/or blots, without using a microscope. And based on detected positional results, locations to be inspected, which include a microscopic-inspecting region, are re-specified on the silicon wafer 2, before being subjected to an actual inspection under the microscope 4. The inspection work can therefore be executed with efficiency, thereby shortening the entire inspection time.

In addition, because the determination whether abnormal (doubtful) luminescent spots are defects or blots precedes an actual inspection under the microscope 4, an erroneous inspection that blots are regarded as being defects is prevented almost completely. An inspection performance of this defect inspection apparatus 1 can therefore be improved to a greater extent.

EXAMPLE

An example will now be described with reference to practical numerical values concerning the defect inspection apparatus 1.

Imaging conditions for the one-dimensional CCD camera 3 includes the number of pixels of 4096 and a scan rate of 1 kHz. As shown in FIG. 4, the width of a field of view of the one-dimensional CCD camera 3 is 210 mm which is in accord with a silicon wafer of 8 inches. The silicon wafer 2 is conveyed by the XY stage 5 at a speed of 50 mm/sec. A linear light source 7 is used as illumination means.

Accordingly, the one-dimensional CCD camera 3 is able to image an object at a resolution of 0.051 (mm/pixel) (=210 (mm)/4096 (pixels)) in its width direction of the field of view.

In the conveyance direction of the silicon wafer 2, a range of 0.05 (mm) (=50 (mm/sec)/1000 (Hz)) can be imaged per one time of scanning carried out by the one-dimensional CCD camera 3. Image signals resultant from each time of scanning are stored in an image memory in the format shown in FIG. 5. If it is desired that the resolution in the conveyance direction is reduced to ½ of that in the width direction of the field of view, the conveyance speed can be increased up to an amount two times larger than the original value or the scanning rate is reduced down to half the original value.

Thus, the one-dimensional CCD camera 3 is able to image the entire area of a surface to be inspected of the silicon wafer 2.

Even when inspecting a specific area of a surface to be inspected of the silicon wafer 2 under the microscope 4 shows that the surface is defective, imaging the surface from a wider field of view may find the fact that only some blots are on the surface. The image processor 6 is able to distinguish such blots from defects depending on their area sizes.

For example, FIG. 6(a) shows a particular region in which luminescent spots gather densely in an entire image of the silicon wafer 2. It can be understood that this particular region represents an OSF occurring at and starting from a location on the silicon wafer 2, due to the fact that any substance touched the location during etching or others. When this particular region is subjected to a magnified inspection under the microscope 4, it should be found that a large number of OSFs occur, as shown in FIG. 6(b). Hence, if only this particular region is inspected, an erroneously inspected result will come out. Other regions, shown as in FIG. 6(c), should be included into the inspection under the microscope 4.

Hence, in this embodiment according to the present invention, the silicon wafer 2 is entirely inspected during the first inspection, so that it can readily be determined whether or not luminescent spots gather in an abnormal state. Through this determination, it is decided that whether a particular region(s) in which luminescent spots gather densely represents a blot(s) or not, and the blot(s) is distinguishably detected in an easier manner.

Practically, the determination will be made on the concept illustrated in FIGS. 7A to 7C. An image read by the one-dimensional CCD camera 3, which is shown in FIG. 7A, is subject to binarization based on a predetermined threshold. Thus, a binary image shown in FIG. 7(b) is obtained, in which a particular region(s) whose pixels having an luminance higher than the threshold are found. This binary image undergoes the selection of an area luminescent distribution(s) whose size(s) is larger than a reference area size previously set for discriminating the distributions, thus only a relatively larger-size luminance distribution(s) being left as a blot(s) on the image, as shown in FIG. 7C. The coordinate of the blot(s) left on the blot-detected image shown in FIG. 7C is then memorized.

A further region is then set, i.e., re-specified, as a microscopic-inspecting region on the surface to be inspected of the silicon wafer 2, with the use of part of the remaining area other than the blot(s) found on the surface. This re-specified region is then subjected to imaging under the microscope 4, during which time the inspection is carried out for possible defects.

(Modification)

(1) There can be provided a variety of modifications derived from the above embodiment. A first modification relates to a relative movement between the silicon wafer 2 and the one-dimensional CCD camera 3 or the microscope 4. In the foregoing embodiment, the XY stage 5 is driven so that the silicon wafer 2 is moved relatively to the one-dimensional CCD camera 3 or the microscope 4, but this configuration is not a definitive list. The combination of the one-dimensional CCD camera 3 and the microscope 4 may be moved relatively to the silicon wafer 2 placed fixedly, whereby the identical operations and advantages to the foregoing can be provided as well.

(2) A second modification is concerned with the camera for imaging the whole area of a surface, section, or others of an object to be inspected. Such a camera is not limited to the one-dimensional camera 3 described in the foregoing embodiment. Alternatively, a two-dimensional CCD camera may be used. If using the two-dimensional CCD camera, it is sufficient that the XY stage 5 on which the silicon wafer 2 is loaded is initially driven to be located immediately under the two-dimensional CCD camera. This eliminates the necessity of moving the XY stage 5 for scanning, unlike the foregoing embodiment, thus simplifying the control of the XY stage 5. This modification also provides the identical operations and advantages to the foregoing embodiment.

(3) A third modification is concerned with the functions realized by the image processor 6. In the foregoing embodiment, the image processor 6 has been configured to function not only as a controller for the XY stage 5 but also as a processor itself for processing image signals. An alternative configuration is that the functions performed by the image processor 6 are assigned to separate units, in which a unit, or controller is in charge of the controlling the operations of the XY stage 5 and the image processor 6 is dedicated to only the operation for processing the image signals. The controller and the image processor 6 are, of course, configured to be information-communicable to each other.

Although the embodiment and modifications described above contain many specificities, these should not be construed as limiting the scope of the present invention but as mealy providing illustrations of some of the presently preferred embodiments of the present invention. The person skilled in the art can alter or modify the present invention into a variety of different other modes without departing from the scope of the appended claims and their equivalents.

What is claimed is:

1. A method of inspecting defects on a surface or section of an object to be inspected, comprising the steps of:

performing a first inspection to image a whole area of the surface or section of the object with an optical device to detect a suspect region including either a defect or a blot from information of the image;

binarizing the image information; and performing a second inspection to conduct a detailed inspection under a microscope with reference to information of the suspect region detected by the first inspection performing step, wherein the first inspection performing step determines that the suspect region is a blot when a distribution of luminance showing the suspect region acquired by binarizing the image information is larger than a predetermined value, and wherein the second inspection performing step avoids the suspect region determined to be a blot and inspects a region other than the determined blot when the detailed inspection is conducted under the microscope.

2. The method according to claim 3, wherein the first inspection performing step includes the step of driving a one-dimensional CCD camera of which the field of view is set to agree with a width of the object to cause a relative movement covering a distance corresponding to a length of the object so as to image a whole area of the surface of the object.

3. An apparatus for inspecting defects on a surface or section of an object to be inspected, comprising:

an optical device which images a whole area of the surface or section of the object and detects a suspect region including either a defect or a blot from information of the image;

means for binarizing the image information;

a microscope for conducting a detailed inspection with reference to information of the suspect region detected by the optical device; and an image processor which determines that the suspect region is a blot when a distribution of luminance showing the suspect region acquired by binarizing the image information imaged by the optical device is larger than a predetermined value, and avoids the region determined to be a blot to inspect a region other than the determined blot when the detailed inspection is conducted under the microscope.

4. The apparatus according to claim 3, wherein the optical device includes a one-dimensional CCD camera of which the field of view is set to agree with a width of the object, the one-dimensional CCD camera configured to cause a relative movement covering a distance corresponding to a length of the object.

* * * * *